United States Patent

Schmidt et al.

[11] 4,021,557
[45] May 3, 1977

[54] 11-AMINOALKYL-PYRIDOBENZODIAZEPINONES AND SALTS THEREOF

[75] Inventors: Günther Schmidt; Günther Engelhardt; Sigfrid Püschmann, all of Biberach an der Riss, Germany

[73] Assignee: Boehringer Ingelheim GmbH, Ingelheim am Rhein, Germany

[22] Filed: Apr. 23, 1975

[21] Appl. No.: 570,805

[30] Foreign Application Priority Data

May 22, 1974 Germany .................. 2424811

[52] U.S. Cl. .................. 424/256; 260/293.59; 260/295 T; 424/267
[51] Int. Cl.² .................. C07D 471/04
[58] Field of Search ... 260/293.59, 295 T, 239.3 T; 424/256, 267

[56] References Cited

UNITED STATES PATENTS

| | | | |
|---|---|---|---|
| 3,316,249 | 4/1967 | Hanze | 260/239.3 |
| 3,634,408 | 1/1972 | Schmidt et al. | 260/239.3 |
| 3,660,380 | 5/1972 | Schmidt et al. | 260/239.3 |

FOREIGN PATENTS OR APPLICATIONS 1,505,795  11/1967  France .................. 260/239.3

OTHER PUBLICATIONS

Burger, Medicinal Chemistry, 3rd Ed., Part II (Wiley-Interscience, N. Y. 1970) pp.1544–1580.
Turner, Screening Methods in Pharmacology, (Academic Press, N. Y. 1965) pp. 238–239.

Primary Examiner—Cecilia M. S. Jaisle
Attorney, Agent, or Firm—Hammond & Littel

[57] ABSTRACT

Compounds of the formula

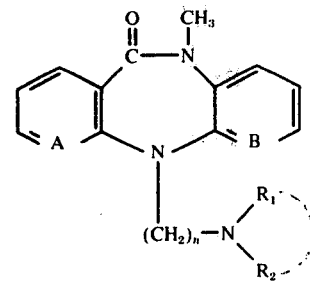

wherein
$R_1$ is hydrogen, straight or branched alkyl of 1 to 3 carbon atoms or benzyl,
$R_2$ is straight or branched alkyl of 1 to 3 carbon atoms, or
$R_1$ and $R_2$, together with each other and the nitrogen atom to which they are attached, are pyrrolidino, piperidino or hexamethyleneimino,
A and B are each nitrogen or methylidenyl (=CH—), but other than both nitrogen or methylidenyl at the same time, and
$n$ is 2 or 3, and non-toxic, pharmacologically acceptable acid addition salts thereof; the compounds as well as the salts are useful as bronchospasmolytics.

26 Claims, No Drawings

11-AMINOALKYL-PYRIDOBENZODIAZEPINONES AND SALTS THEREOF

This invention relates to novel 11-aminoalkyl-pyridobenzodiazepinones and acid addition salts thereof, as well as to various methods of preparing these compounds.

More particularly, the present invention relates to a novel class of pyridobenzodiazepinones represented by the formula

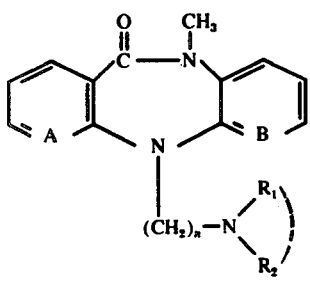

wherein
  $R_1$ is hydrogen, straight or branched alkyl of 1 to 3 carbon atoms or benzyl,
  $R_2$ is straight or branched alkyl of 1 to 3 carbon atoms, or
  $R_1$ and $R_2$, together with each other and the nitrogen atom to which they are attached, are pyrrolidino, piperidino or hexamethyleneimino,
  A and B are each nitrogen or methylidenyl (=CH—), but other than both nitrogen or methylidenyl at the same time, and
  n is 2 or 3,
and non-toxic, pharmacologically acceptable acid addition salts thereof.

The compounds embraced by formula I above may be prepared by the following methods.

Method A

By reacting an alkali metal salt of a pyridobenzodiazepinone of the formula

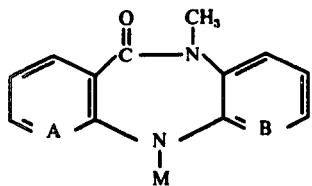

wherein A and B have the meanings previously defined, and M is an alkali metal, with an amine of the formula

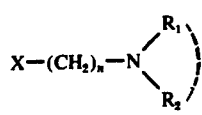

wherein $R_1$, $R_2$ and n have the meanings previously defined, and X is a reactive ester component of an inorganic or strong organic acid, such as halogen or tosyl. The reaction is performed in an inert organic solvent at a temperature between 20 and 250° C. Examples of suitable inert solvents are xylene, toluene, dioxane, dimethylformamide or acetone.

The alkali metal salt of the formula II is advantageously formed in situ in the reaction mixture just before the reaction is performed, for example, by reacting sodium hydroxide, potassium hydroxide, lithium hydroxide, sodium hydride, potassium hydride or sodium amide with an 11-unsubstituted pyridobenzodiazepinone of the formula II, that is, wherein M is hydrogen.

Method B

By reacting a pyridobenzodiazepinone of the formula

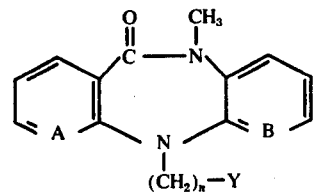

wherein A, B and n have the meanings previously defined, and Y is halogen, preferably chlorine, or tosyl, with an amine of the formula

wherein $R_1$ and $R_2$ have the meanings previously defined.

The reaction is carried out in an inert organic solvent at a temperature between −20° and +20° C. Examples of suitable inert solvents are xylene, toluene, dioxane, dimethylformamide or acetone.

In those instances where method A or B yields a compound of the formula I wherein $R_1$ is benzyl, this compound may, if desired, be converted into the corresponding compound wherein $R_1$ is hydrogen by removal of the benzyl group by hydrogenation with catalytically activated hydrogen. The hydrogenation is performed at a temperature between 20 and 100° C and a hydrogen pressure between 1 and 100 atmospheres in the presence of a noble metal catalyst, such as palladium-on-charcoal.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, maleic acid, fumaric acid, citric acid, tartaric acid, malic acid, 8-chlorotheophylline or the like.

A pyridobenzodiazepinone starting compound of the formula II, wherein A is =CH—, B is nitrogen and M is hydrogen, may be prepared by reacting a 2-halo-3-amino-pyridine of the formula

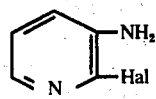

wherein Hal is halogen, with an acid halide of o-nitrobenzoic acid of the formula

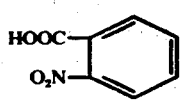  (VII)

in an inert solvent, such as benzene or toluene, in the presence of a hydrohalic acid-binding agent, such as an alkali metal carbonate, a trialkyl amine or pyridine, at temperatures up to the boiling point of the particular solvent which is used. First, an amide of the formula

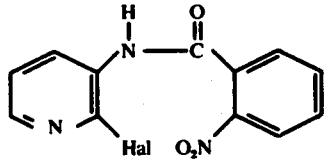  (VIII)

is obtained, which is then reduced with catalytically activated hydrogen at a temperature between 20° and 100° C with a metal or tin chloride in the presence of an inorganic acid, whereby a compound of the formula

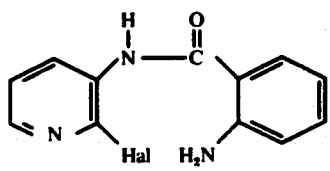  (IX)

is obtained, which is subsequently cyclized by heating it to a temperature of 200° C or higher.

The reduction of the compound of formula VIII is performed in an inert solvent, such as methanol, ethanol or dioxane, preferably by means of hydrogen in the presence of Raney nickel at a temperature of 50° C and under pressure.

The ring closure of the compound of the formula IX to form 5,11-dihydro-6H pyrido[2,3-b][1,4]benzodiazepin-6-one of the formula

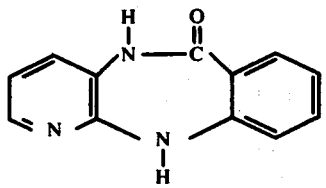  (X)

is optionally carried out in the presence of a high-boiling point solvent, such as paraffin oil or decahydronaphthalene, and optionally in the presence of a basic catalyst, such as potassium carbonate, or in the presence of copper powder.

The compound of the formula X is converted into the corresponding starting compound of the formula II, wherein M is hydrogen, by treatment with methyl iodide in hot ethanol in the presence of sodium hydroxide (see also German Pats. No. 1,179,943 and 1,204,680).

A pyridobenzodiazepinone starting compound of the formula II, wherein A is nitrogen, B is =CH— and M is hydrogen, may be obtained by reacting a 2-halo-nicotinic acid of the formula

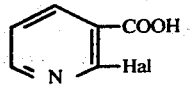  (XI)

wherein Hal is halogen, with o-phenylenediamine of the formula

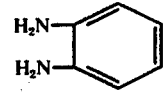  (XII)

at temperatures above 150° C, optionally in the presence of an inert, high-boiling-point solvent, such as tetrahydronaphthalene, dichloro- or trichloro-benzene or glycol, and of an inert gas, whereby first 6,11-dihydro-5H-pyrido[2,3-b][1,5]benzodiazepin-5-one of the formula

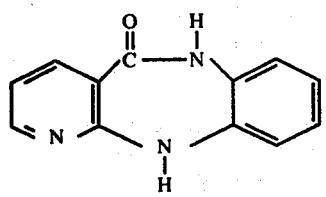  (XIII)

is obtained, which is subsequently converted into the corresponding pyridobenzodiazepinone of the formula II, wherein M is hydrogen, by means iodide in ethanol in the presence of sodium hydroxide by refluxing for 4 hours (see also German Pats. No. 1,238,479 and 1,251,767).

A pyridobenzodiazepinone of the formula IV may be obtained by reacting an alkali metal salt of a corresponding pyridobenzodiazepinone of the formula II, i.e. for example in the presence of sodium hydride or sodium hydroxide, with a dihalo-alkane, such as with 1-bromo-3-chloro-propane, preferably in the presence of an inert solvent at room temperature.

The starting compounds of the formulas III and V are described in the literature or may be prepared by methods described in the literature.

The following examples illustrate the present invention and will enable others skilled in the art to understand it more completely. It should be understood, however, that the invention in not limited solely to the particular examples given below.

EXAMPLE 1

11-(3'-Diethylamino-n-propyl)-6,11-dihydro-6-methyl-5H-pyrido[2,3-b][1,5]benzodiazepin-5-one and its hydrochloride by method A A mixture of 4.52 gm (0.02 mol) of 6,11-dihydro-6-methyl -5H-pyrido[2,3-b][1,5]benzodiazepin-5-one, 7.0 gm (0.175 mol) of pulverized sodium hydroxide, 50 ml of acetone and 12 ml of 3-diethylamino-n-propyl chloride was refluxed for 2 hours. Thereafter, the still hot reaction mixture was suction-filtered, and the filtrate was evaporated in vacuo. The residue was shaken with a mixture of acetic acid and ether, the acidic aqueous phase was isolated and made alkaline with concentrated ammonia, and the oil precipitated thereby was extracted with ether. After evaporation of the ether extract, the oily residue was distilled, yielding 76% of theory of the compound of the formula

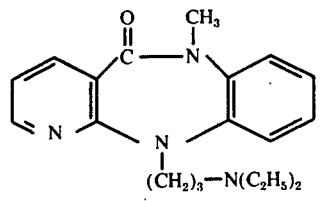

which had a boiling point of 198°–200° C. at 0.14 mm Hg.

The base thus obtained was dissolved in dioxane, the solution was acidified with concentrated hydrochloric acid, and the precipitate formed thereby was collected and recrystallized from isopropanol, yielding the hydrochloride which had a melting point of 206°–208° C.

EXAMPLE 2

11-(2'-Dimethylamino-ethyl)-6,11-dihydro-6-methyl-5H-pyrido[2,3-b][1,5]benzodiazepin-5-one by method A 9.0 gm of 6,11-dihydro-6-methyl-5H-pyrido[2,3-b][1,5]benzodiazepin-5-one were dissolved in 200 ml of hot absolute xylene, 2.1 gm of 50% sodium hydride in mineral oil were added to the solution, and the mixture was refluxed for 2 hours. Then, 5.3 gm of 2-dimethylamino-ethyl chloride were added dropwise, and the mixture was refluxed for 16 hours more. The cooled reaction mixture was shaken with a mixture of ether and water, and the organic phase was separated and extracted with dilute acetic acid. Then the acidic aqueous layer was made alkaline with concentrated ammonia, and the precipitated oil was extracted with ether. After evaporation of the ether extract, the residue was distilled, yielding 7.0 gm (59% of theory) of 11-(2'-dimethylamino-ethyl)-6,11-dihydro-6-methyl-5H-pyrido[2,3-b][1,5]benzodiazepin-5-one, b.p. 163°–164° C. at 0.01 mm Hg.

EXAMPLE 3

11-(2'-Methylamino-ethyl)-6,11-dihydro-6-methyl-5H-pyrido [2,3-b][1,5]benzodiazepin-5-one (a) 18.1 gm (0.08 mol) of 6,11-dihydro-6-methyl-5H-pyrido[2,3-b][1,5]benzodiazepin-5-one were dissolved in 180 ml of dimethylformamide at room temperature, 2.88 gm (0.096 mol) of 80% sodium hydride in mineral oil were added to the solution, and the mixture was stirred at 60° C. for 45 minutes. Then, 17.7 gm (0.096 mol) of 2-(N-benzyl-methylamino)-ethyl chloride were added dropwise, and the resulting mixture was stirred at 120° C. for 30 minutes. After evaporation in vacuo, the residue was dissolved in chloroform/dilute acetic acid, and the aqueous phase was separated and made alkaline with concentrated ammonia. The base, which precipitated as an oil, was taken up in chloroform, the solvent was distilled off in vacuo and the oily residue was distilled, yielding 22.4 gm (75% of theory) of 11-[2'-N-benzyl-methylamino)-ethyl]-6,11-dihydro-6-methyl-5-H-pyrido [2,3-b][1,5]benzodiazepin-5-one, b.p. 212°–216° C. at 0.05 mm Hg.

b. 13.5 gm of this substance were dissolved in 175 ml of methanol, and hydrogenated with palladized coal at 50° C. and 50 atmospheres. After separating the catalyst, the reaction mixture was evaporated in vacuo, and the oily residue was purified by column chromatography (silicagel, eluant: chloroform + methanol + n-pentane + concentrated ammonia = 68+15+15+2). After distillation of the evaporated eluate (b.p. 184°–186° C. at 0.07 mm Hg), 4.5 gm of 11-(2'-methylamino-ethyl)-6,11-dihydro-6-methyl-5H-pyrido[2,3-b][1,5]benzodiazepin-5-one were obtained. Yield: 22% of theory.

EXAMPLE 4

11-(2'-Dimethylamino-ethyl)-5,11-dihydro-5-methyl 6H-pyrido [2,3-b][1,4]benzodiazepin-6-one 9.0 gm of 5,11-dihydro-5-methyl-6H-pyrido[2,3-b][1,4]benzodiazepin-6-one were dissolved in 200 ml of hot absolute xylene, 2.1 gm of 50% sodium hydride in mineral oil were added to the solution, and the mixture was refluxed for two hours. Then, 5.3 gm of 2-dimethylamino-ethyl chloride were added dropwise, and the resulting mixture was refluxed for 16 hours more. The cooled reaction mixture was taken up with a mixture of ether and water, and the organic phase was separate and extracted with dilute acetic acid. Then, the acidic aqueous extract was made alkaline with concentrated aqueous ammonia, and the precipitated oil was extracted with ether. After evaporation of the ether, the residue was distilled, yielding 5.4 gm of 11-(2-dimethylaminoethyl)-5,11-dihydro-5-methyl-6H-pyrido[2,3-b][1,4]benzodiazepin-6-one, b.p. 171°–173° C. at 0.006 mm Hg. After crystallization and recrystallization from petroleum ether, 3.2 gm of the substance, m.p. 109°–110° C., were obtained.

EXAMPLE 5

Using a procedure analogous to that described in Example 2, 11-[3'-(N-ethyl-N-isopropylamino)-n-propyl]-6,11-dihydro-6-methyl-5H-pyrido[2,3-b][1,5]benzodiazepin-5-one, b.p. 185°–187° C. at 0.05 mm Hg, was prepared from 6,11-dihydro-6-methyl-5H-pyrido[2,3-b][1,5]benzodiazepin-5-one and 3-(N-ethyl-isopropylamino)-n-propyl chloride.

EXAMPLE 6

Using a procedure analogous to that described in Example 2, 11-(3'-diisopropylamino-n-propyl)-6,11-dihydro-6-methyl-5H-pyrido[2,3-b][1,5]benzodiazepin-5-one, b.p. 200°–203° C. at 0.08 mm Hg, was prepared from 6,11-dihydro-6-methyl-5H-pyrido[2,3-b][1,5]benzodiazepin-5-one and 3-diisopropylamino-n-propyl chloride.

EXAMPLE 7

Using a procedure analogous to that described in Example 2, 6,11-dihydro-11-(2'-dimethylamino-ethyl)-6-methyl-5H-pyrido[2,3-b][1,5]benzodiazepin-5-one, b.p. 163°–164° C. at 0.01 mm Hg, was prepared from 6,11-dihydro-6-methyl-5H-pyrido[2,3-b][1,5]-benzodiazepin-5-one and 2-dimethylamino-ethyl chloride.

EXAMPLE 8

Using a procedure analogous to that described in Example 2, 6,11 -dihydro-11-(3'-dimethylamino-n-propyl)-6-methyl-5H-pyrido[2,3-b][1,5]benzodiazepin-5-one, b.p. 180°–183° C. at 0.03 mm Hg, was prepared from 6,11-dihydro-6-methyl5H-pyrido[2,3-b][1,5]benzodiazepin-5-one and 3-dimethylamino-n-propyl chloride.

EXAMPLE 9

Using a procedure analogous to that described in Example 3, 6,11-dihydro-6-methyl-11-(3'-methylamino-n-propyl)-5H-pyrido[2,3-b][1,5]benzodiazepin-5-one, b.p. 182° C. at 0.05 mm Hg, was prepared from 6,11-dihydro-6-methyl-5H-pyrido[2,3-b][1,5]benzodiazepin-5-one and 3-(N-benzyl-methylamino)-n-propyl chloride.

EXAMPLE 10

Using a procedure analogous to that described in Example 3, 11-(3'-ethylamion-n-propyl)-6,11-dihydro-6-methyl-5H-pyrido[2,3-b][1,5]benzodiazepin-5one, b.p. 193°–195° C. at 0.12 mm Hg, was prepared from 6,11-dihydro-6-methyl-5H-pyrido[2,3-b][1,5]benzodiazepin-5-one and 3-(N-benzylethylamino)-n-propyl chloride.

EXAMPLE 11

Using a procedure analogous to that described in Example 3, 6,11-dihydro-11-(3'-isopropylamino-n-propyl)-6-methyl-5H-pyrido[2,3-b][1,5]benzodiazepin-5-one, b.p. 183°–185° C. at 0.05 mm Hg, was prepared from 6,11-dihyro-6-methyl-5H-pyrido[2,3-b][1,5]benzodiazepin-5-one and 3-(N-benzyl-isopropylamino)-n-propyl chloride.

EXAMPLE 12

Using a procedure analogous to that described in Example 2, 11-(2'-diethylamino-ethyl)-6,11-dihydro-6-methyl-5H-pyrido[2,3-b][1,5]benzodiazepin-5-one, b.p. 183°–186° C. at 0.06 mm Hg, was prepared from 6,11-dihydro-6-methyl-5H-pyrido[2,3-b][1,5]benzodiazepin-5-one and 2-diethylaminoethyl chloride.

EXAMPLE 13

Using a procedure analogous to that described in Example 2, 6,11-dihydro-11-(3'-di-n-propylamino-n-propyl)-6-methyl-5H-pyrido[2,3-b][1,5]benzodiazepin-5-one, b.p. 192°–195° C. at 0.04 mm Hg, was prepared from 6,11-dihydro-6-methyl-5H-pyrido[2,3-b][1,5]benzodiazepin-5-one and 3-di-n-propylamino-n-propyl chloride.

EXAMPLE 14

Using a procedure analogous to that described in Example 2, 6,11-dihydro-11-(2'-diisopropylamino-ethyl)-6-methyl-5H-pyrido[2,3-b][1,5]benzodiazepin-5-one, b.p. 188°–191° C. at 0.07 mm Hg, was prepared from 6,11-dihydro-6-methyl-5H-pyrido[2,3-b][1,5]benzodiazepin-5-one and 2-dissopropylamino-ethyl chloride.

EXAMPLE 15

Using a procedure analogous to that described in Example 2, 6,11-dihydro-6-methyl-11-(3'-pyrrolidion-n-propyl)-5H-pyrido[2,3-b][1,5]benzodiazepin-5-one, b.p. 203°–206° C. at 0.15 mm Hg, was prepared from 6,11-dihydro-6-methyl-5H-pyrido[2,3-b][1,5]benzodiazepin-5-one and 3-pyrrolidino-n-propyl chloride.

EXAMPLE 16

Using a procedure analogous to that described in Example 2, 6,11-dihydro-6-methyl-11-(3'-piperidino-n-propyl)-5H-pyrido[2,3-b][1,5]benzodiazepin-5-one, b.p. 200°–202° C. At 0.09 mm Hg, was prepared from 6,11-dihydro-6-methyl-5H-pyrido[2,3-b][1,5]benzodiazepin-5-one and 3-piperidino-n-propyl chloride.

EXAMPLE 17

Using a procedure analogous to that described in Example 2, 6,11-dihydro-11-(3'-hexamethyleneimino-n-propyl)-6-methyl-5H-pyrido[2,3-b][1,5]benzodiazepin-5-one, b.p. 238°–242° C. at 0.05 mm Hg, was prepared from 6,11-dihydro-6-methyl-5H-pyrido[2,3-b][1,5]benzodiazepin-5-one and 3-hexamethyleneimino-n-propyl chloride.

EXAMPLE 18

Using a procedure analogous to that described in Example 2, 6,11-dihydro-6-methyl-11-(2'-pyrrolidinoethyl)-5H-pyrido[2,3-b][1,5]benzodiazepin-5-one, b.p. 183°–185° C. at 0.06 mm Hg, was prepared from 6,11-dihydro-6-methyl-5H-pyrido[2,3-b][1,5]benzodiazepin-5-one and 2-pyrrolidino-ethyl chloride.

EXAMPLE 19

Using a procedure analogous to that described in Example 4, 11-(2'-diethylamino-ethyl)-5,11-dihydro-methyl-6H-pyrido[2,3-b][1,4]benzodiazepin-6-one, b.p. 197°–199° C. at 0.07 mm Hg, of the formula

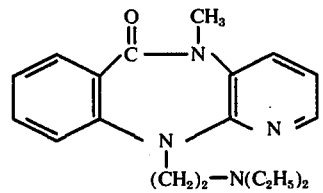

was prepared from 5,11-dihydro-5-methyl-6H-pyrido[2,3-b][1,4]benzodiazepin-6-one and 2-diethylamino-ethyl chloride.

EXAMPLE 20

Using a procedure analogous to that described in Example 4, 5,11-dihydro-11-(2'-diisopropylamino-ethyl)-5-methyl-6H-pyrido[2,3-b][1,4]benzodiazepin-6-one, b.p. 196°–199° C. at 0.07 mm Hg, was prepared from 5,11-dihydro-5-methyl-6H-pyrido[2,3-b][1,4]benzodiazepin-6-one and 2-diisopropylamino-ethyl chloride.

EXAMPLE 21

Using a procedure analogous to that described in Example 4, 5,11-dihydro-11-(3'-dimethylamino-n-propyl)-5-methyl-6H-pyrido[2,3-b][1,4]benzodiazepin-6-one, b.p. 202°–205° C. at 2.5 mm Hg, was prepared from 5,11-dihydro-5-methyl-6H-pyrido[2,3-b][1,4]benzodiazepin-6-one and 3-dimethylamino-n-propyl chloride.

EXAMPLE 22

Using a procedure analogous to that described in Example 4, 5,11-dihydro-11-(3'-diethylamino-n-propyl)-5-methyl-6H-pyrido[2,3-b][1,4]benzodiazepin-6-one, b.p. 212°–214° C. at 0.2 mm Hg, was prepared from 5,11-dihydro-5-methyl-6H-pyrido[2,3-b][1,4]benzodiazepin-6-one and 3-diethylamino-n-propyl chloride.

EXAMPLE 23

Using a procedure analogous to that described in Example, 4, 5,11-dihydro-11-(3'-diisopropylamino-n-propyl)-5-methyl-6H-pyrido[2,3-b][1,4]benzodiazepin-6-one, b.p. 217°–220° C. at 0.1 mm Hg, was prepared from 5,11-dihydro-5-methyl-6H-pyrido[2,3-b][1,4]benzodiazepin-6-one and 3-diisopropylamino-n-propyl chloride.

EXAMPLE 24

Using a procedure analogous to that described in Example 4, 5,11-dihydro-5-methyl-11-(3'-pyrrolidino-n-propyl)-6H-pyrido[2,3-b][1,4]benzodiazepin-6-one, m.p. 119°–121° C., was prepared from 5,11-dihydro-5-methyl-6H-pyrido[2,3-b][1,4]benzodiazepin-6-one and 3-pyrrolidino-n-propyl chloride.

Its hydrochloride, obtained by dissolving the base in dioxane and acidifying the solution with ethereal hydrochloric acid, had a melting point of 218°–221° C. (recrystallized from isopropanol).

EXAMPLE 25

Using a procedure analogous to that described in Example 4, 5,11-dihydro-5-methyl-11-(3'-piperidino-n-propyl)-6H-pyrido[2,3-b][1,4]benzodiazepin-6-one, b.p. 198°–200° C. at 0.06 mm Hg, was prepared from 5,11-dihydro-5-methyl-6H-pyrido[2,3-b][1,4]benzodiazepin-6-one and 3-piperidino-n-propyl chloride.

EXAMPLE 26

Using a procedure analogous to that described in Example 4, 5,11-dihydro-11-(3'-hexamethyleneimino-n-propyl)-5-methyl-6H-pyrido[2,3-b][1,4]benzodiazepin-6-one, b.p. 195°–198° C. at 0.06 mm Hg, was prepared from 5,11-dihydro-5-methyl-6H-pyrido[2,3-b][1,4]benzodiazepin-6-one and 3-hexamethyleneimino-n-propyl chloride.

EXAMPLE 27

11-(3'-Dimethylamino-n-propyl)-6,11-dihydro-6-methyl-5H-pyrido[2,3-b][1,5]benzodiazepin-5-one by method A A mixture of 4.5 gm of 6,11-dihydro-6-methyl-5H-pyrido[2,3-b][1,5]benzodiazepin-5-one, 0.83 gm of 55% sodium hydride in mineral oil, and 100 ml of absolute xylene was refluxed for two hours. Thereafter, 7 gm of p-toluenesulfonic acid 3-dimethylamino-n-propyl ester were added, and the resulting mixture was refluxed for 14 hours more. After cooling, the reaction mixture was suction-filtered, and the filtrate was extracted with dilute acetic acid. From the acidic aqueous phase, the base was precipitated as an oil with concentrated ammonia and taken up in ether. After evaporation of the ether solution, the residue was distilled, yielding 2.4 gm of 11(3'-dimethylamino-n-propyl)-6,11-dihydro-6-methyl-5H-pyrido[2,3-b][1,5]benzodiazepin-5-one, b.p. 180°–183° C. at 0.03 mm Hg, which melted at 98.5°–100° C. after crystallization from cyclohexane and recrystallization from petroleum ether.

The compounds of the present invention, that is, those embraced by formula I above and their non-toxic pharmacologically acceptable acid addition salts, have useful pharmacodynamic properties. More particularly, they exhibit very effective bronchospasmolytic activities in warm-blooded animals, such as guinea pigs, and are therefore indicated for the treatment of bronchial asthma.

The compounds of the present invention have the decisive advantage over the β-receptor-mimetics usually employed in case of this inication in that the tachycardiac side-effects associated with β-receptor-mimetics are completely absent. In the case of the β-receptor-mimetics these side-effects lead to unpleasant subjective discomforts, even when they are used as directed, and in case of accidental over-dosing they may produce serious complications, such as heart muscle necroses.

Moreover, in contrast to β-receptor-mimetics, the compounds of the present invention not only effect a relaxation of the spastic bronchial musculature in the asthmatic subject, but also produce a liquefying effect on any tenaceous mucus which may be present as an additional obstacle in the respiratory tract. In other words, the compounds of this invention also exhibit expectorant activity.

The above pharmacodynamic activities of the compounds of the instant invention, as well as their acute toxicities, were ascertained by the standard pharmacological test methods described below, and the results for a few representative species of the genus are shown in Tables I-III, where A = 11-(3'-diethylamino-n-propyl)-6,11-dihydro-6-methyl-5H-pyrido[2,3-b][1,5]benzodiazepin-5-one hydrochloride, B = 6,11-dihydro-11-(2'-dimethylamino-ethyl)-6-methyl-5H-pyrido[2,3-b][1,5]benzodiazepin-5-one hydrochloride, C = 6,11-dihydro-11-(3'-dimethylamino-n-propyl)-6-methyl-5H-pyrido[2,3-b][1,5]benzodiazepin-5-one hydrochloride, D = 6,11-dihydro-6-methyl-11-(3'-methylamino-n-propyl)-5H-pyrido[2,3-b][1,5]benzodiazepin-5-one hydrochloride, E = 11-(3'-ethylamino-n-propyl)-6,11-dihydro-6-methyl-5H-pyrido[2,3b][1,5]benzodiazepin-5-one hydrochloride, F = 6,11-dihydro-11-(3'-isopropylamino-n-propyl)-6-methyl-5H-pyrido[2,3-b][1,5]benzodiazepin-5one hydrochloride, G = 11-(2'-diethylamino-ethyl)-6,11-dihydro-6-methyl-5H-pyrido[2,3-b][1,5]benzodiazepin-5-one hydrochloride, H = 6,11-dihydro-11-(3'-di-n-propylamino-n-propyl)-6-methyl5H-pyrido[2,3-b][1,5]benzodiazepin-5-one hydrochloride, I = 6,11-dihydro-11-(2'-diisopropylamino-ethyl)-6-methyl-5H-pyrido[2,3-b][1,5]benzodiazepin-5-one hydrochloride, J = 6,11-dihydro-11-(3'-diisopropylamino-n-propyl)-6-methyl-5H-pyrido[2,3-b][1,5]benzodiazepin-5one hydrochloride, K = 11-[3'-(N-ethyl-N-isopropyl-amino)-n-propyl]-6,11-dihydro-6-methyl-5H-pyrido[2,3-b][1,5]benzodiazepin-5-one hydrochloride, L = 6,11-dihydro-6-methyl-11-(3'-pyrrolidino-n-propyl)-5H-pyrido[2,3-b][1,5]benzodiazepin-5one hydrochloride, M = 6,11-dihydro-6-methyl-11-(3'-piperidino-n-propyl)-5H-pyrido[2,3-b][1,5]benzodiazepin-5-one hydrochloride, N = 6,11-dihydro-11-(3'-hexamethyleneimino-n-propyl)-6-methyl-5H-pyrido[2,3-b][1,5]benzodiazepin-5-one hydrochloride, O = 6,11-dihydro-6-methyl-11-(2'-pyrrolidino-ethyl)-5H-pyrido[2,3-b][1,5]benzodiazepin-5-one hydrochloride, P = 11-(2'-diethylamino-ethyl)-5,11-dihydro-5-methyl-6H-pyrido[2,3-b][1,4]benzodiazepin-6-one hydrochloride, Q = 5,11-dihydro-11-(2'-diisopropylamino-ethyl)-5-methyl-6H-pyrido[2,3-b][1,4]benzodiazepin-6-one hydrochloride, R = 5,11-dihydro-11-(3'-dimethylamino-n-propyl)-5-methyl6H-pyrido[2,3-b][1,4]benzodiazepin-6-one, S = 5,11-dihydro-11-(3'-diethylamino-n-propyl)-5-methyl-6H-pyrido[2,3-b][1,4]benzodiazepin-6-one hydrochloride, T = 5,11-dihydro-11-(3'-diisopropylamino-n-propyl)-5-methyl-6H-pyrido[2,3-b][1,4]benzodiazepin-6-one hydrochloride, U = 5,11-dihydro-5-methyl-11-(3-pyrrolidino-n-propyl)-6H-pyrido[2,3-b][1,4]benzodiazepin-6-one hydrochloride, V = 5,11-dihydro-5-methyl-11-(3'-piperidino-n-propyl)-6H-pyrido[2,3-b][1,4]benzodiazepin-6-one hydrochloride, and W = 5,11-dihydro-11-(3'-hexamethyleneimino-n-propyl)-5-methyl-6H-pyrido[2,3-b][1,4]benzodiazepin-6-one hydrochloride.

Methods

The antiasthmatic activity was tested as the antagonism to bronchospasm provoked by intravenous administration of 20γ of acetylcholine per kg body weight in anesthetized guinea pigs (according to method of Konzett and Rossler). From the average percentage decrease of the bronchospasm produced by administering various doses of the compound of the percent invention an $ED_{50}$ was determined by graphic extrapolation. The compounds were administered intravenously.

The acute toxicity was determined with NMRI-mice of both sexes (body weight 20 gm) after intravenous administration of the compound. 0.1 ml of a 0.9% sodium chloride solution per 10gm of animal was used as the vehicle. The $LD_{50}$ was calculated from the percentage of animals which died within a period of 14 days after administration of various doses, according to the method of Litchfield and Wilcoxon.

The effect on the heart rate was tested on cats of both sexes (body weight between 2.3 and 3.5 kg) under chloralose-urethane anesthesia. The heart rate was continuously registered by means of a Grass-tachograph 7P4, controlled by the R-wave of the electrocardiogram. The test compound was injected through a catheter introduced into the vena femoralis.

The expectorant activity was ascertained by the method of Perry et al, J. Pharmcol. exp. Therap. 73, 65 (1941), as modified by Engelhorn et al, Arzneim. Forsch. 21, 1045 (1971), on male guinea pigs (body weight from 450 to 550 gm), which has been anesthetized by intraperitoneal injection of a 25% urethane solution (1.0 gm/kg). The test compound was administered orally at the indicated dosage levels, each in 2 ml of distilled water, by means of an esophageal tube. 5 tests per dose. The increase in secretion was calculated from the quantity of fluid secreted over a period of 2 hours after administration of the test compound, as compared to the quantity secreted without administration of the test compound.

TABLE I

| Compound | Bronchospasmolytic $ED_{50}$ against acetylcholine-induced bronchospasm γ/kg i.v. | Average duration of effective action in the $ED_{50}$ range in minutes | $LD_{50}$ in the mouse after i.v. application mgm/kg | Confidence limits (95% probability) |
|---|---|---|---|---|
| A | 31 | >130 | 62.3 | 58.1 – 66.8 |
| B | 148 | >110 | 25.8 | 22.1 – 30.2 |
| C | 81 | >60 | 30.7 | 28.2 – 33.5 |
| D | 155 | 45 | 43.2 | 38.6 – 48.4 |
| E | 68 | >90 | 56.1 | 53.5 – 58.9 |
| F | 172 | >110 | 43.5 | 38.5 – 49.2 |
| G | 44 | 50 | 27.1 | 25.1 – 29.3 |
| H | 95 | >70 | 21.7 | 20.3 – 23.2 |
| I | 18 | 40 | 30.3 | 28.6 – 32.1 |
| J | 16.5 | 50 | 22.6 | 20.8 – 24.6 |
| K | 20 | >80 | 30.0 | 27.3 – 33.0 |
| L | 43 | 120 | 22.7 | 21.6 – 23.9 |
| M | 63 | >60 | 10.6 | 9.9 – 11.3 |
| N | 64 | >50 | 12.7 | 11.4 – 14.1 |
| O | 97 | >30 | 11.4 | 9.9 – 13.1 |
| P | 210 | 110 | | |
| Q | 53 | >50 | 27.0 | 24.1 – 30.3 |
| R | 190 | >50 | | |
| S | 123 | >110 | | |
| T | 16.5 | 50 | 22.2 | 21.0 – 23.4 |
| U | 105 | >50 | 22.9 | 21.4 – 24.5 |
| V | 180 | >110 | 13.4 | 12.2 – 14.7 |
| W | 215 | >40 | 13.4 | 12.2 – 14.7 |

TABLE II

Effect on heart rate of the anesthetized cat after intravenous administration

| Compound | tested dosage range γ/kg i.v. | type of the reaction * | $ED_{10}$** γ/kg | $ED_{25}$** γ/kg |
|---|---|---|---|---|
| A | 12.5 – 16,000 | — | 2,100 | >16,000 |
| C | 250 – 4,000 | — | >4,000 | |
| E | 250 – 4,000 | — | 1,050 | > 4,000 |
| I | 250 – 4,000 | — | 1,300 | > 4,000 |
| J | 250 – 4,000 | — | 1,950 | > 4,000 |
| K | 250 – 4,000 | — | 1,350 | > 4,000 |
| L | 250 – 4,000 | — | 1,900 | 3,950 |
| M | 250 – 4,000 | — | 1,400 | > 4,000 |
| O | 250 – 4,000 | — | >4,000 | |
| T | 250 – 4,000 | — | 1,400 | 3,600 |
| U | 250 – 4,000 | — | 2,300 | > 4,000 |
| V | 250 – 4,000 | — | 1,100 | > 4,000 |

TABLE II-continued

Effect on heart rate of the anesthetized cat after intravenous administration

| Compound | tested dosage range γ/kg i.v. | type of the reaction * | $ED_{10}$** γ/kg | $ED_{25}$** γ/kg |
|---|---|---|---|---|
| W | 125 – 4,000 | — | 1,200 | > 4,000 |

*—= decrease in heart rate
**dose leading to a 10 or 25% alteration of the heart rate, determined by graphic extrapolation.

TABLE III

Secretolytic activity

TABLE III

| Compound | Secretolytic activity Dose γ/kg | φpercent change in quantity of secretion |
|---|---|---|
| A | 5 | + 114 |
|   | 0.5 | + 80 |
| K | 0.5 | + 113 |
| J | 0.5 | + 108 |

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effect bronchospasmolytic dosage unit of the compounds according to the present invention is from 0.083 to 84 γ/kg body weight, preferably 0.83 to 8.4 γ/kg, and the daily dose is from 0.00025 to 0.25 mgm/kg, preferably 0.0025 to 0.025 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 29

Tablets

The tablet composition is compounded from the following ingredients:

| | |
|---|---|
| 11-(3'-Diethylamino-n-propyl)-6,11-dihydro-6-methyl-5H-pyrido[2,3-b][1,5]benzodiazepin-5-one hydrochloride | 0.05 parts |
| Corn starch | 75.00 parts |
| Lactose | 49.95 parts |
| Polyvinyl pyrrolidone | 4.00 parts |
| Magnesium stearate | 1.00 parts |
| Total | 130.00 parts |

Preparation

The corn starch and the lactose are intimately admixed, and the mixture is homogeneously moistened with an aqueous solution of the pyriobenzodiazepinone and polyvinyl pyrrolidone. The moist mass is granulated through a 1.5 mm- mesh screen, dried at 45° C and again passed through the screen. The dry granulate thus obtained is mixed with the magnesium stearate, and the composition is compressed into 130-mgm tablets in a conventional tablet making machine. Each tablet contains 0.05 mgm of pyridobenzodiazepinone compound and is an oral dosage unit composition with effective bronchospasmolytic action.

EXAMPLE 30

Coated pills

The pill core composition is compounded from the following ingredients:

| | |
|---|---|
| 11-(3'-Diethylamino-n-propyl)-6,11-dihydro-6-methyl-5H-pyrido[2,3-b][1,5]benzodiazepin-5-one hydrochloride | 0.5 parts |
| Calcium acid phosphate, anhydrous | 34.0 parts |
| Corn starch | 9.5 parts |
| Gelatin | 2.0 parts |
| Talcum | 4.0 parts |
| Total | 50.0 parts |

Preparation

The pyridobenzodiazepinone is intimately admixed with the corn starch and the calcium acid phosphate, and the mixture is moistened with an aqueous solution of the gelatin and granulated through a 1.5 mm-mesh screen, dried at 45° C and again passed through the screen. The dry granulate thus obtained is admixed with the talcum, and the composition is compressed into 50 mgm-pill cores, which are then coated with a thin shell consisting essentially of a mixture of sugar and talcum and finally polished with beeswax. Each coated pill contains 0.5 mgm of the pyridobenzodiazepinone compound and is an oral dosage unit composition with effective bronchospasmolytic action.

EXAMPLE 31

Gelatin capsules

The capsule filler composition is compounded from the following ingredients:

| | |
|---|---|
| 11-(3'-Diethylamino-n-propyl)-6,11-dihydro-6-methyl-5H-pyrido[2,3-b][1,5]benzoidiazepin-5-one hydrochloride | 0.020 parts |
| Corn starch | 79.980 parts |
| Colloidal silicic acid | 3.000 parts |
| Magnesium stearate | 2.000 parts |
| Total | 85.000 parts |

Preparation

An aqueous solution of the pyridobenzodiazepinone salt is sprayed onto the colloidal silicic acid, the mixture is dried and intimately admixed with the other ingredients, and 85 mgm-portions of the composition are filled into gelatin capsules of suitable size. Each capsule contains 20 γ of the pyridobenzodiazepinone salt and is an oral dosage unit composition with effective bronchospasmolytic action.

EXAMPLE 32

Suppositories

The suppository composition is compounded from the following ingredients:

| | |
|---|---|
| 11-(3'-Diethylamino-n-propyl)-6,11-dihydro-6-methyl-5H-pyrido[2,3-b][1,5]benzodiazepin-5-one hydrochloride | 0.2 parts |
| Suppository base (e.g. cocoa butter) | 1699.3 parts |

-continued

| | Total | 1700.0 parts |
|---|---|---|

Preparation

The suppository base is melted and cooled to 38° C, the milled pyridobenzodiazepinone salt is homogeneously dispersed therein, the mixture is cooled to 35° C and 1700 mgm-portions thereof and poured into cooled suppository molds and allowed to harden therein. Each suppository contains 0.2 mgm of the pyridobenzodiazepinone salt and is a rectal dosage unit composition with effective bronchospasmolytic action.

EXAMPLE 33

Solution

The solution is compounded from the following ingredients:

| | |
|---|---|
| 11-(3'-Diethylamino-n-propyl)-6,11-dihydro-6-methyl-5H-pyrido[2,3-b][1,5]benzodiazepin-5-one hydrochloride | 0.001 parts |
| Carboxymethyl cellulose | 0.1 parts |
| Methyl p-hydroxy-benzoate | 0.05 parts |
| Propyl p-hydroxy-benzoate | 0.01 parts |
| Cane sugar | 10.0 parts |
| Glycerin | 5.0 parts |
| Sorbitol solution, aqueous, 70% | 20.0 parts |
| Flavoring | 0.3 parts |
| Distilled water    c.s.ad | 100.0 parts by vol. |

Preparation

The distilled water is heated to 70° C, and the p-hydroxybenzoates, the glycerin and carboxymethyl cellulose are dissolved therein, while stirring. The solution is cooled to room temperature, and the pyridobenzodiazepinone salt is added while stirring and dissolved therein. After addition of the sugar, sorbitol solution and flavoring, the solution is evacuated for de-aeration while stirring. 5 ml of the solution contain 0.05 mgm of the pyridobenzodiazepinone salt and are an oral dosage unit composition with effective bronchospasmolytic action.

EXAMPLE 34

Aerosol

The aerosol is compounded from the following ingredients:

| | |
|---|---|
| 11-(3'-Diethylamino-n-propyl)-6,11-dihydro-6-methyl-5H-pyrido[2,3-b][1,5]benzodiazepin-5-one hydrochloride | 7.5 parts |
| Ethanol | 997.5 parts |
| Propellant mixture | 8,395.0 parts |
| Total | 9,900.0 parts |

Preparation

The pyridobenzodiazepinone salt is dissolved in the ethanol, the solution is cooled to −30° C and filled into correspondingly cooled aerosol cans, the propellant mixture at −50° C is added, and the cans are closed with a metering valve which expels a quantity of aerosol containing 0.05 mgm of the pyridobenzodiazepinone salt with each actuation. The aerosol is an inhalation dosage unit composition with effective bronchospasmolytic action.

Analogous results are obtained when any one of the other pyridobenzodiazepinones embraced by formula I or a non-toxic, pharmacologically acceptable acid addition salt thereof is substituted for the particular pyridobenzodiazepinone salt in Examples 29 through 24. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention of the scope of the appended claims.

We claim:
1. A compound of the formula

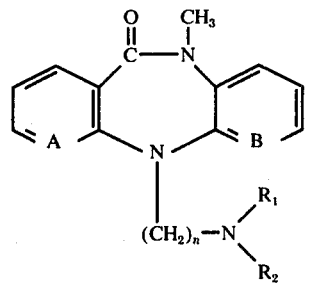

wherein
$R_1$ is hydrogen, alkyl of 1 to 3 carbon atoms or benzyl,
$R_2$ is alkyl of 1 to 3 carbon atoms, or
$R_1$ and $R_2$, together with each other and the nitrogen atom to which they are attached, are pyrrolidino, piperidino or hexamethyleneimino,
A and B are each nitrogen or =CH—, but other than both nitrogen or =CH— at the same time, and
$n$ is 2 to 3,
or a non-toxic, pharmacologically acceptable acid addition salt thereof.

2. A compound of claim 1, which is 11-(3'-diethylamino-n-propyl)-6,11-dihydro-6-methyl-5H-pyrido[2,3-b][1,5]benzodiazepin-5-one or a non-toxic, pharmacologically acceptable acid addition salt thereof.

3. A compound of claim 1, which is 6,11-dihydro-11-(2'-dimethylamino-ethyl)-6-methyl-5-H-pyrido[2,3-b][1,5]benzodiazepin-5-one or a non-toxic, pharmacologically acceptable acid addition salt thereof.

4. A compound of claim 1, which is 6,11-dihydro-11-(3'-dimethylamino-n-propyl)-6-methyl-5H-pyrido[2,3-b][1,5]benzodiazepin-5-one or a non-toxic, pharmacologically acceptable acid addition salt thereof.

5. A compound of claim 1, which is 6,11-dihydro-6-methyl-11-(3'-methylamino-n-propyl)-5H-pyrido[2,3-b][1,5]benzodiazepin-5-one or a non-toxic, pharmacologically acceptable acid addition salt thereof.

6. A compound of claim 1, which is 11-(3'-ethylamino-n-propyl)-6,11-dihydro-6-methyl-5H-pyrido[2,3-b][1,5]benzodiazepin-5-one or a non-toxic, pharmacologically acceptable acid addition salt thereof.

7. A compound of claim 1, which is 6,11-dihydro-11-(3'-isopropylamino-n-propyl)-6-methyl-5H-pyrido[2,3-b][1,5]benzodiazepin-5-one or a non-toxic, pharmacologically acceptable acid addition salt thereof.

8. A compound of claim 1, which is 11-(2'-diethylamino-ethyl)-6,11-dihydro-6-methyl5H-pyrido[2,3-b][1,5]benzodiazepin-5-one or a non-toxic, pharmacologically acceptable acid addition salt thereof.

9. A compound of claim 1, which is 6,11-dihydro-11-(3'-di-n-propylamino-n-propyl)-6-methyl-5H-pyrido[2,3-b][1,5]benzodiazepin-5-one or a non-toxic, pharmacologically acceptable acid addition salt thereof.

10. A compound of claim 1, which is 6,11-dihydro-11-(2'-diisopropylamino-ethyl)-6-methyl-5H-pyrido[2,3-b][1,5]benzodiazepin-5-one or a non-toxic, pharmacologically acceptable acid addition salt thereof.

11. A compound of claim 1, which is 6,11-dihydro-11-(3'-diisopropylamino-n-propyl)-6-methyl-5H-pyrido[2,3-b][1,5]benzodiazepin-5-one or a non-toxic, pharmacologically acceptable acid addition salt thereof.

12. A compound of claim 1, which is 11-[3'-(N-ethyl-N-isopropylamino)-n-propyl]-6,11-dihydro-6-methyl-5H-pyrido[2,3-b][1,5]benzodiazepin-5-one or a non-toxic, pharmacologically acceptable acid addition salt thereof.

13. A compound of claim 1, which is 6,11-dihydro-6-methyl-11-(3'-pyrrolidino-n-propyl)-5H-pyrido[2,3-b][1,5]benzodiazepin-5-one or a non-toxic, pharmacologically acceptable acid addition salt thereof.

14. A compound of claim 1, which is 6,11-dihydro-6-methyl-11-(3'-piperidino-n-propyl)-5H-pyrido[2,3-b][1,5]benzodiazepin-5-one or a non-toxic, pharmacologically acceptable acid addition salt thereof.

15. A compound of claim 1, which is 6,11-dihydro-11-(3'-hexamethyleneimino-n-propyl)-6-methyl-5H-pyrido[2,3-b][1,5]benzodiazepin-5-one or a non-toxic, pharmacologically acceptable acid addition salt thereof.

16. A compound of claim 1, which is 6,11-dihydro-6-methyl-11-(2'-pyrrolidino-ethyl)-5H-pyrido[2,3-b][1,5]benzodiazepin-5-one or a non-toxic, pharmacologically acceptable acid addition salt thereof.

17. A compound of claim 1, which is 11-(2'-diethylamino-ethyl)-5,11-dihydro-5-methyl-6H-pyrido[2,3-b][1,5]benzodiazepin-6-one or a non-toxic, pharmacologically acceptable acid addition salt thereof.

18. A compound of claim 1, which is 5,11-dihydro-11-(2'-diisopropylamino-ethyl)-5-methyl-6H-pyrido[2,3-b][1,4]benzodiazepin-6-one or a non-toxic, pharmacologically acceptable acid addition salt thereof.

19. A compound of claim 1, which is 5,11-dihydro-11-(3'-dimethylamino-n-propyl)-5-methyl-6H-pyrido[2,3-b][1,4]benzodiazepin-6-one or a non-toxic, pharmacologically acceptable acid addition salt thereof.

20. A compound of claim 1, which is 5,11-dihydro-11-(3'-diethylamino-n-propyl)-5-methyl-6H-pyrido[2,3-b][1,4]benzodiazepin-6-one or a non-toxic, phamacologically acceptable acid addition salt thereof.

21. A compound of claim 1, which is 5,11-dihydro-11-(3'-diisopropylamino-n-propyl)-5-methyl-6H-pyrido[2,3-b][1,4]benzodiazepin-6-one or a non-toxic, pharmacologically acceptable acid addition salt thereof.

22. A compound of claim 1, which is 5,11-dihydro-5-methyl-11-(3'-pyrrolidino-n-propyl)-6H-pyrido[2,3-b][1,4]benzodiazepin-6-one or a non-toxic, pharmacologically acceptable acid addition salt thereof.

23. A compound of claim 1, which is 5,11-dihydro-5-methyl-11-(3'-piperidino-n-propyl)-6H-pyrido[2,3-b][1,4]benzodiazepin-6-one or a non-toxic, pharmacologically acceptable acid addition salt thereof.

24. A compound of claim 1, which is 5,11-dihydro-11-(3'-hexamethyleneimino-n-propyl)-5-methyl-6H-pyrido[2,3-b][1,4]benzodiazepin-6-one or a non-toxic, pharmacologically acceptable acid addition salt thereof.

25. A bronchospasmolytic pharmaceutical dosage unit composition consisting essentially of an inert pharmaceutical carrier and an effective bronchospasmolytic amount of a compound of claim 1.

26. The method of relieving bronchial spasms in a warm-blooded animal in need of such treatment, which comprises administering to said animal an effective bronchospasmolytic amount of a compound of claim 1.

* * * * *

UNITED STATES PATENT OFFICE
CERTIFICATE OF CORRECTION

Patent No. 4,021,557     Dated May 3, 1977

Inventor(s) GUNTHER SCHMIDT, GUNTHER ENGELHARDT & SIGFRID PUSCHMANN

It is certified that error appears in the above-identified patent and that said Letters Patent are hereby corrected as shown below:

Col. 7, line 28 - "-dihyro-" should read -- -dihydro- -- line 60 - "-pyrrolidion-" should read -- -pyrrolidino- --

Col. 10, line 5 - "inication" should read --indication--

Col. 13, line 63 - "pyriobenzodiazepinone" should read --pyriodobenzodiazepinone--

Col. 15, line 30 - "c.s.ad" should read --q.s.ad-- line 56 - "8,395.0 parts" should read --8,895.0 parts--

Col. 16, line 8 - "24" should read --34--

Col. 18, line 5 - "[1,5]" should read --[1,4]--

Signed and Sealed this second Day of August 1977

[SEAL]

Attest:

RUTH C. MASON
Attesting Officer

C. MARSHALL DANN
Commissioner of Patents and Trademarks